(12) United States Patent
Terada

(10) Patent No.: US 12,329,622 B2
(45) Date of Patent: Jun. 17, 2025

(54) NONWOVEN FABRIC AND METHOD FOR PRODUCING SAME

(71) Applicants: JNC CORPORATION, Tokyo (JP); JNC FIBERS CORPORATION, Tokyo (JP)

(72) Inventor: Hirokazu Terada, Shiga (JP)

(73) Assignees: JNC CORPORATION, Tokyo (JP); JNC FIBERS CORPORATION, Tokyo (JP)

( * ) Notice: Subject to any disclaimer, the term of this patent is extended or adjusted under 35 U.S.C. 154(b) by 0 days.

(21) Appl. No.: 18/278,002

(22) PCT Filed: Mar. 1, 2022

(86) PCT No.: PCT/JP2022/008545
§ 371 (c)(1),
(2) Date: Aug. 20, 2023

(87) PCT Pub. No.: WO2022/202142
PCT Pub. Date: Sep. 29, 2022

(65) Prior Publication Data
US 2024/0139040 A1    May 2, 2024

(30) Foreign Application Priority Data
Mar. 23, 2021   (JP) ................. 2021-048081

(51) Int. Cl.
*A61F 13/511*   (2006.01)
*A61F 13/15*   (2006.01)
(Continued)

(52) U.S. Cl.
CPC ....... *A61F 13/51121* (2013.01); *D04H 1/541* (2013.01); *D10B 2401/022* (2013.01);
(Continued)

(58) Field of Classification Search
None
See application file for complete search history.

(56) References Cited

U.S. PATENT DOCUMENTS

2009/0130939 A1* 5/2009 Kimura .............. D04H 1/43828
442/364
2019/0055684 A1* 2/2019 Koizumi .............. D04H 1/5412

FOREIGN PATENT DOCUMENTS

| JP | H06330443 | 11/1994 | |
| JP | 2019080907 | 5/2019 | |
| WO | WO-2017170791 A1 * | 10/2017 | ........... D04H 1/4326 |

OTHER PUBLICATIONS

"International Search Report (Form PCT/ISA/210) of PCT/JP2022/008545", mailed on Apr. 26, 2022, with English translation thereof, pp. 1-4.

* cited by examiner

*Primary Examiner* — Ha S Nguyen
(74) *Attorney, Agent, or Firm* — JCIPRNET

(57) ABSTRACT

The present invention addresses the problem of providing a nonwoven fabric that is bulky, has excellent softness, and has high strength. Provided is a nonwoven fabric in which the points at which heat fusible composite fibers intersect with each other are fused by heat. The nonwoven fabric has a high-density-side surface layer where the fiber density is 5 to 20 fibers/mm². The ratio of the fiber density of the high-density-side surface layer and the fiber density of a low-density-side surface layer of the nonwoven fabric is 1.4 or less. The strength per unit basis weight of the nonwoven fabric is 0.40 N/50 mm or greater.

8 Claims, 2 Drawing Sheets

(51) Int. Cl.
  *A61F 13/51* (2006.01)
  *D04H 1/541* (2012.01)
(52) U.S. Cl.
  CPC .. *D10B 2401/063* (2013.01); *D10B 2403/022* (2013.01); *D10B 2509/026* (2013.01)

HIGH-DENSITY-SIDE SURFACE LAYER          LOW-DENSITY-SIDE SURFACE LAYER

HIGH-DENSITY-SIDE SURFACE LAYER 
LOW-DENSITY-SIDE SURFACE LAYER

NONWOVEN FABRIC AND METHOD FOR PRODUCING SAME

CROSS-REFERENCE TO RELATED APPLICATION

This application is a 371 application of the International PCT application serial no. PCT/JP2022/008545, filed on Mar. 1, 2022, which claims the priority benefits of Japanese Patent Application No. 2021-048081, filed on Mar. 23, 2021. The entirety of each of the above-mentioned patent applications is hereby incorporated by reference herein and made a part of this specification.

TECHNICAL FIELD

The present invention relates to a nonwoven fabric that is bulky, has excellent softness, and has high strength, and a method for producing the same.

BACKGROUND ART

Nonwoven fabrics used in absorbent articles such as disposable diapers and sanitary napkins are required to have greater comfortableness and thus are continuously being improved. In particular, in a surface material for absorbent articles such as diapers, the following are required: excellent bulkiness and softness; no occurrence of lint and no damage due to rubbing against a skin surface; a performance (liquid permeability) to quickly send liquids to absorbers with respect to various liquids with different viscosities such as urine, soft feces, and menstrual blood, and solid materials; and the like.

A through-air nonwoven fabric is known as a nonwoven fabric used for surface materials of absorbent articles and the like. The through-air nonwoven fabric is obtained by heat-treating a web composed of composite fibers constituted of at least two types of thermoplastic resins having different melting points. As a method of heat-treating a web, for example, a method of fusing composite fibers to each other by heat using a heat treatment device (for example, a hot air current penetration type heat treatment machine, and a hot air current blowing type heat treatment machine) equipped with a conveying support that supports and conveys a web is known. However, because the through-air nonwoven fabric is produced by blowing a hot air current, pressure is applied to a web by the hot air current, which results in a reduction in bulk of the nonwoven fabric and the formation of a high fiber density side and a low fiber density side in the thickness direction, and by this formation of a high-density-side surface layer, a problem of impairment of softness and a problem of clogging of high-viscosity components such as soft feces and menstrual blood are caused.

Patent Literature 1 discloses use of a through-air nonwoven fabric to prevent clogging of high-viscosity liquids by using a low density side as a skin side. However, although the use of such a nonwoven fabric improves the liquid permeability with respect to high-viscosity liquids, bulkiness and softness are not sufficient, and a nonwoven fabric that satisfies all of such requirements has not yet been obtained.

Meanwhile, there is a known aperture nonwoven fabric in which apertures are formed by piercing the nonwoven fabric with heated needles of a needle roll while sandwiching the nonwoven fabric between the needle roll and a perforated roll that receives it (for example, Patent Literature 2). Patent Literature 2 discloses that a three-dimensional shape is imparted by pinching and conveying a nonwoven fabric between a pin roll having a large number of pins arranged on its surface and a protrusion roll having protrusions for forming shapes between pin rows. However, when using this method, because the nonwoven fabric is sandwiched between the rolls and crushed, there is a problem in that the nonwoven fabric is compressed in portions other than aperture portions, resulting in impairment of bulkiness and softness. In addition, although the liquid permeability of the apertures is certainly high, there is a problem in that liquid return tends to occur easily.

CITATION LIST

Patent Literature

[Patent Literature 1]
  Japanese Patent Laid-Open No. 2019-80907
[Patent Literature 2]
  Japanese Patent Laid-Open No. H6-330443

SUMMARY OF INVENTION

Technical Problem

In view of these circumstances, an objective of the present invention is to provide a nonwoven fabric that is bulky, has excellent softness, and has high strength so that lint and damage do not occur.

Solution to Problem

The inventors of the present invention thought that the above-mentioned objective can be achieved by producing a nonwoven fabric by heat fusion of fibers in a state of maintaining the shape of a web, that is, in a state in which the level of a fiber density is small in the thickness direction of the nonwoven fabric. Therefore, an attempt was made to set the speed of a hot air current as low as possible in a heat fusion step to reduce the pressure of the hot air current blowing onto the web surface. However, it became clear that a reduction in hot air current speed lowers the speed stability, which increases the variation in physical properties of the obtained nonwoven fabric, thereby further reducing the strength of the nonwoven fabric significantly. In addition, to ameliorate the variations in physical properties and a reduction in strength, it was required to lengthen a hot air current treatment time, which caused a problem of a significant decrease in productivity. In view of these circumstances, the inventors of the present invention examined further processing methods. As a result, it was found that by fusing points at which heat fusible composite fibers intersect with each other by heat under no pressure using superheated steam gas, a nonwoven fabric that is bulky, has excellently softness, and has high strength can be obtained, thereby completing the present invention by which the above-mentioned objective is achieved.

In other words, the present invention has the following configurations.

[1] A nonwoven fabric in which points at which heat fusible composite fibers intersect with each other are fused by heat, the nonwoven fabric containing: a high-density-side surface layer having a fiber density of 5 to 20 fibers/mm$^2$, in which a ratio of the fiber density of the high-density-side surface layer and a fiber density of a low-density-side surface layer of the nonwoven fabric is 1.4 or less, and a strength per unit basis weight of the nonwoven fabric is 0.40 N/50 mm or greater.

[2] The nonwoven fabric according to [1], in which a specific volume is 100 cm$^3$/g or greater.

[3] The nonwoven fabric according to [1] or [2], in which a compression work amount at a maximum compression load of 4 gf/cm$^2$ is 0.20 gf·cm/cm$^2$ or greater.

[4] The nonwoven fabric according to any one of [1] to [3], in which a fineness of the heat fusible composite fiber is 0.8 to 20 dtex.

[5] The nonwoven fabric according to any one of [1] to [4], in which a fiber length of the heat fusible composite fiber is 20 to 102 mm.

[6] A method for producing a nonwoven fabric, the method including: a step of forming a web containing heat fusible composite fibers; and a step of fusing points at which the heat fusible composite fibers intersect with each other by heat under no pressure using superheated steam gas.

[7] The method for producing a nonwoven fabric according to [6], in which the step of forming the web is a carding method or an airlaid method.

[8] The method for producing a nonwoven fabric according to [6] or [7], further including a step of heat-treating after the step of fusing the heat fusible composite fibers by heat.

[9] An absorbent article using the nonwoven fabric according to any one of [1] to [5].

Advantageous Effects of Invention

According to the present invention, a nonwoven fabric that is bulky, has excellent softness, and has high strength can be provided. In addition, the nonwoven fabric that is bulky, has excellent softness, and has high strength can be produced with high productivity. Furthermore, in addition to the bulkiness, excellent softness, and no occurrence of lint and damage in such a nonwoven fabric, the liquid permeability with respect to highly viscous liquids is also expected to be improved, which makes the nonwoven fabric able to be suitably used as a surface material for absorbent articles such as diapers, for example.

DESCRIPTION OF EMBODIMENTS

Figure 1:
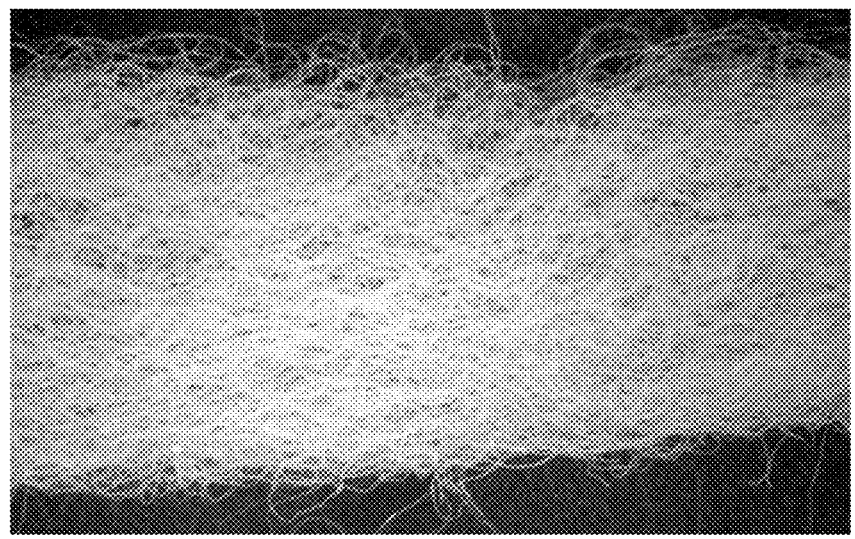
FIG. 1 is an optical micrograph of a cross-section of a nonwoven fabric according to an example of the present invention.

A nonwoven fabric of the present invention in which points at which heat fusible composite fibers intersect with each other are fused by heat is characterized by containing a high-density-side surface layer having a fiber density of 5 to 20 fibers/mm$^2$, in which a ratio of the fiber density of the high-density-side surface layer and a fiber density of a low-density-side surface layer is 1.4 or less, and a strength per unit basis weight of the nonwoven fabric is 0.40 N/50 mm or greater.

(Heat Fusible Composite Fiber)

The heat fusible composite fiber used in the nonwoven fabric of the present invention is not particularly limited as long as it can be melted by heat to form a fusion point. Examples thereof include concentric sheath-core heat fusible composite fibers, eccentric sheath-core heat fusible composite fibers, and side-by-side heat fusible composite fibers. In addition, the cross-sectional shape of the heat fusible composite fiber is not particularly limited, and it is possible to use any of round shapes such as circles and ovals, polygonal shapes such as triangles and squares, variant shapes such as star shapes and eight lotus petal shapes, or shapes with splits or hollows.

A thermoplastic resin constituting the heat fusible composite fiber is not particularly limited, and examples thereof include polyethylene resins such as low-density polyethylene (LDPE), linear low-density polyethylene (LLDPE), and high-density polyethylene (HDPE); polypropylene resins such as crystalline polypropylene (PP), and copolymers (Co-PP) of propylene and ethylene or α-olefins which contain propylene as a main component; and polyester resins such as polyethylene terephthalate (PET), polybutylene terephthalate, and polyester copolymers (Co-PET). The combination of the thermoplastic resins constituting the heat fusible composite fiber is not particularly limited, but a melting point difference is preferably 10° C. or higher, and is more preferably 20° C. or higher. Examples of specific combinations of high melting point component/low melting point component of the thermoplastic resin include PP/HDPE, PP/Co-PP, PET/HDPE, PET/LLDPE, PET/Co-PET, and PET/PP, but from the viewpoint of bulkiness, raw material cost, production stability, and the like, a combination of PP/HDPE or PET/HDPE is preferable, and a combination of PET/HDPE is more preferable. In addition, from the viewpoint of the heat fusibility of the heat fusible composite fiber, the low melting point component preferably accounts for 50% or more, and more preferably accounts for 70% or more of the surface of the composite fiber. Furthermore, the volume fraction of the low melting point component and the high melting point component is not particularly limited, but is preferably 20/80 to 80/20, and is more preferably 30/70 to 70/30. When there is 20% by volume or more of the low-melting thermoplastic resin, the fusion point strength of the heat fusible composite fiber is improved, which is preferable because then a high-strength nonwoven fabric can be obtained. When there is 80% by volume or less of the low-melting thermoplastic resin, this is preferable because then a soft and bulky nonwoven fabric can be obtained.

As necessary, the thermoplastic resin constituting the heat fusible composite fiber may contain additives such as antioxidants, light stabilizers, ultraviolet absorbers, neutralizing agents, nucleation agents, epoxy stabilizers, lubricants, antibacterial agents, deodorants, flame retardants, antistatic agents, pigments, and plasticizers, within the range not impairing the effects of the present invention.

The fineness of the heat fusible composite fiber used in the nonwoven fabric of the present invention is not particularly limited, but is preferably 0.8 to 20 dtex, is more preferably 0.9 to 10 dtex, and is further preferably 1.0 to 6.0 dtex. In particular, when used as a surface material for absorbent articles such as disposable diapers, the softness of the nonwoven fabric becomes favorable by further lowering the fineness of the heat fusible composite fiber. Furthermore, when the fineness is low, smoothness is improved, thereby reducing friction with the skin and reducing rashes. In general, a nonwoven fabric containing heat fusible composite fibers having a low fineness has an increased number of constitution fibers, making it difficult for a hot air current to pass through. As a result, wind pressure is applied to the entire nonwoven fabric, and the bulk decreases. However, since the nonwoven fabric of the present invention uses superheated steam gas instead of the hot air current for heat fusion of fibers, a web can be thoroughly fused by heat without applying pressure, which makes it possible to obtain a nonwoven fabric having an excellent sensation on the skin in addition to high bulkiness and high strength.

The fiber length of the heat fusible composite fiber used in the nonwoven fabric of the present invention is not particularly limited, but is preferably 20 to 102 mm, and is more preferably 30 to 51 mm. When the fiber length is 20 to 102 mm, this is preferable because then a web having excellent opening properties and texture is easily formed in a web formation step by a carding method or the like, making it possible to obtain a nonwoven fabric having uniform physical properties.

The nonwoven fabric of the present invention may contain fibers, which are not so-called heat fusible composite fibers (hereinafter referred to as "non-heat fusible fibers"), such as natural fibers (such as wood fibers), regenerated fibers (such as rayon), semi-synthetic fibers (such as acetate), chemical fibers, and synthetic fibers (such as polyester, acrylic, nylon, and vinyl chloride), in addition to the heat fusible composite fibers. The term "non-heat fusible fiber" refers to a fiber that does not undergo thermal change (melting or softening) which relates to heat fusion in a heat fusion step performed when producing nonwoven fabrics. When the non-heat fusible fibers are contained, the ratio of the non-heat fusible fibers to the total weight of the nonwoven fabric is not limited as long the effects of the present invention are not hindered. The ratio can be set to 1% to 30% by weight, and is preferably 3% to 15% by weight, for example. When the ratio of the non-heat fusible fibers is 1% by weight or more, an effect suitable for use can be obtained, and when the ratio is 30% by weight or less, a high-strength nonwoven fabric can be obtained.

In addition, on the surfaces of the heat fusible composite fibers and the non-heat fusible fibers, various fiber treatment agents may be provided, as a result of which functions such as hydrophilicity, durable hydrophilicity, water repellency, antistatic properties, surface smoothness, and abrasion resistance may be imparted.

(Nonwoven Fabric)

The nonwoven fabric of the present invention in which points at which the heat fusible composite fibers intersect with each other are fused by heat is characterized by containing the high-density-side surface layer having a fiber density of 5 to 20 fibers/mm$^2$, in which the ratio of the fiber density of the high-density-side surface layer and the fiber density of the low-density-side surface layer is 1.4 or less, and the strength per unit basis weight of the nonwoven fabric is 0.40 N/50 mm or greater. As in the related art, in a method of blowing a hot air current to perform heat fusion of points at which heat fusible composite fibers intersect with each other, depending on fibers used and a production method, it was possible to satisfy 5 to 20 fibers/mm$^2$ as the fiber density of a high-density-side surface layer of a nonwoven fabric, and satisfy 0.40 N/50 mm or more as the strength per unit basis weight. However, in such a nonwoven fabric, the ratio of the fiber density of the high-density-side surface layer and the fiber density of a low-density-side surface layer exceeded 1.4, and satisfactory softness was not obtained. In addition, in a method of blowing a hot air current as slowly as possible, it was possible to satisfy 5 to 20 fibers/mm$^2$ as the fiber density of the high-density-side surface layer of the nonwoven fabric, and satisfy 1.4 or less as the ratio of the fiber density of the high-density-side surface layer and the fiber density of the low-density-side surface layer. However, the strength per unit basis weight was less than 0.40 N/50 mm, which was a low strength, thereby causing lint and damage. In addition, in a method of a compression treatment with hot rolls or the like, it was possible to satisfy 1.4 or less as the ratio of the fiber density of the high-density-side surface layer and the fiber density of the low-density-side surface layer, and satisfy 0.40 N/50 mm or more as the strength per unit basis weight. However, the fiber density exceeded 20 fibers/mm$^2$, and satisfactory bulkiness was not obtained. In contrast, in the present invention, it was found that, by fusing the heat fusible composite fibers by heat under no pressure using superheated steam gas, it is possible to obtain the nonwoven fabric in which the fiber density of the high-density-side surface layer of the nonwoven fabric is 5 to 20 fibers/mm$^2$, the ratio of the fiber density of the high-density-side surface layer and the fiber density of the low-density-side surface layer is 1.4 or less, and the strength per unit basis weight is 0.40 N/50 mm or greater.

The term "surface layer" in the present specification will be described. In the present specification, the "surface layer" means a region corresponding to 20% of the thickness of the entire nonwoven fabric from the surface of the nonwoven fabric toward the center in the thickness direction. In addition, when the fiber density of the surface layers on both sides of the nonwoven fabric is measured, the surface layer on the high fiber density side is referred to as the "high-density-side surface layer", and the surface layer on the low fiber density side is referred to as the "low-density-side surface layer".

Next, the term "fiber density" in the present specification will be described. In the present specification, the "fiber density" is represented by the number of fibers per unit area in the cross section of the nonwoven fabric, and the unit can be fibers/mm$^2$, for example. As for a method for measuring the fiber density, a method using a laser microscope will be described in detail in examples. However, in addition to the method employed in the examples, there is no particular limitation as long as the fiber density can be calculated by a method by identifying the number of fibers present in a certain area in the cross section of the nonwoven fabric, such as a method using a reflective type optical microscope and a method using a scanning electron microscope.

To obtain a bulky nonwoven fabric, it is important that the fiber density of the high-density-side surface layer of the nonwoven fabric of the present invention is 5 to 20 fibers/mm$^2$. When the fiber density of the high-density-side surface layer is 5 fibers/mm$^2$ or more, the number of fibers in contact with each other is sufficient, which makes it possible to obtain a high-strength nonwoven fabric. Meanwhile, when the fiber density is 20 fibers/mm$^2$ or less, the fibers are not too dense, which makes it possible to obtain sufficient bulkiness. From this viewpoint, the fiber density of the high-density-side surface layer is preferably 6 to 18 fibers/mm$^2$, and is more preferably 8 to 16 fibers/mm$^2$. In addition, the fiber density of the low-density-side surface layer may be 3.6 to 20 fibers/mm$^2$ such that the ratio of the fiber density of the high-density-side surface layer and the fiber density of the low-density-side surface layer satisfies 1.4 or less.

It is important that the ratio of the fiber density of the high-density-side surface layer and the fiber density of the low-density-side surface layer of the nonwoven fabric of the present invention is 1.4 or less to obtain a nonwoven fabric having excellent softness. When the ratio of the fiber density of the high-density-side surface layer and the fiber density of the low-density-side surface layer is 1.4 or less, the fiber density of the high-density-side surface layer does not become too large, which makes it possible to prevent a decrease in softness. From this viewpoint, the ratio of the fiber density of the high-density-side surface layer and the fiber density of the low-density-side surface layer is preferably 1.3 or less, and is more preferably 1.2 or less. The lower limit value of the ratio of the fiber density of the high-density-side surface layer and the fiber density of the low-density-side surface layer is 1.0. The closer it gets to 1.0, this means that a state approaches the state in which the fiber density of the high-density-side surface layer and the fiber density of the low-density-side surface layer are equal, that is, the ideal state in the present invention.

To obtain a high-strength nonwoven fabric that does not cause lint and damage, it is important that the strength per unit basis weight of the nonwoven fabric of the present invention is 0.40 N/50 mm or more, preferably 0.50 N/50 mm or more, and more preferably 0.60 N/50 mm or more. The upper limit of the strength per unit basis weight is not particularly limited, but is practically 3 N/50 mm or less in consideration of a balance between the bulkiness of the nonwoven fabric.

The specific volume of the nonwoven fabric of the present invention is not particularly limited, but is preferably 100 $cm^3/g$ or more, is more preferably 110 $cm^3/g$ or more, and is further preferably 120 $cm^3/g$ or more. When the specific volume is 100 $cm^3/g$ or more, the bulkiness of the nonwoven fabric can be made satisfied. The upper limit of the specific volume is not particularly limited, but is practically 300 $cm^3/g$ or less in consideration of a balance between the strength of the nonwoven fabric.

The basis weight of the nonwoven fabric is not particularly limited, but is preferably 10 to 100 $g/m^2$, and is more preferably 15 to 70 $g/m^2$. In particular, the basis weight is preferably 15 to 40 $g/m^2$ when the nonwoven fabric is used as a surface material for absorbent articles such as diapers. When the basis weight is 15 $g/m^2$ or more, this is preferable because then the return of liquids such as urine, soft feces, and menstrual blood can be prevented, and when the basis weight is 40 $g/m^2$ or less, this is preferable because then air permeability is favorable.

The compression work amount of the nonwoven fabric of the present invention is not particularly limited, but is preferably 0.20 gf $cm/cm^2$ or greater, and is more preferably 0.20 to 0.50 gf $cm/cm^2$ at a maximum compression load of 4 $gf/cm^2$. The compression work amount is a measure of the softness of the nonwoven fabric, and it can be evaluated that the greater the compression work amount, the better the softness. When the compression work amount is 0.20 gf $cm/cm^2$ or greater, satisfactory softness can be obtained, and by using as a surface material for absorbent articles such as diapers, it is possible to obtain absorbent articles having an excellent wearing feeling.

The nonwoven fabric of the present invention may consist of one type of (single layer) nonwoven fabric, or may be a laminate of two or more types of nonwoven fabrics having different fineness, compositions, densities, and the like. When two or more types of nonwoven fabrics are laminated, for example, by laminating nonwoven fabrics having different fineness, a nonwoven fabric in which the size of the gap formed between the fibers changes in the thickness direction of the nonwoven fabric is formed, which makes it possible to control liquid permeability, a liquid permeation speed, the texture of a surface layer, and the like. Furthermore, for example, by laminating nonwoven fabrics having different compositions, a nonwoven fabric in which the hydrophilicity and the hydrophobicity of the nonwoven fabric change in the thickness direction of the nonwoven fabric is formed, which makes it possible to control liquid permeability and a liquid permeation speed.

In addition, there is no particular limitation, but the nonwoven fabric of the present invention may be laminated and integrated with nonwoven fabrics, films, or sheets obtained by another method such as a through-air nonwoven fabric, a spunbond nonwoven fabric, a melt-blown nonwoven fabric, a spunlace nonwoven fabric, a needle-punched nonwoven fabric, films, meshes, and nets. By laminating and integrating, liquid permeability, a liquid permeation speed, liquid return properties, and the like can be controlled. A method of laminating and integrating is not particularly limited, but examples thereof include a method of laminating and integrating using an adhesive such as hot melt, and a method of laminating and integrating by thermal adhesion such as through-air or heat embossing.

Within a range not impairing the effects of the present invention, the nonwoven fabric may be subjected to antistatic processing, water repellent processing, hydrophilic processing, antibacterial processing, ultraviolet absorption processing, near-infrared absorption processing, electret processing, or the like depending on the purpose.

(Method for Producing Nonwoven Fabric)

A method for producing a nonwoven fabric of the present invention includes: a step of forming a web containing the heat fusible composite fibers (hereinafter sometimes referred to as a web formation step); and a step of fusing points at which the heat fusible composite fibers intersect with each other by heat under no pressure using superheated steam gas (hereinafter sometimes referred to as a heat fusion step). According to this method, the points at which the fibers intersect with each other can be fused by heat while maintaining the shape of the web, that is, while being in a state with a small crude density in the thickness direction, and thereby a nonwoven fabric that is bulky, has excellent softness, and has high strength can be obtained. In the step of fusing, by heat, points at which heat fusible composite fibers intersect with each other by blowing a hot air current, which has been used in the related art, when the hot air current speed is reduced, the heat fusion between the fibers becomes insufficient, which inevitably makes the strength of the nonwoven fabric low. Although not bound by any specific theory, it is thought that because the superheated steam gas used in the present invention has a larger heat capacity than the hot air current, heat is sufficiently and thoroughly transmitted to the web even under no pressure, which makes it possible to form a firm heat fusion point, as a result of which a nonwoven fabric that is bulky, has excellent softness, and has high strength can be produced with high productivity.

The web containing the heat fusible composite fibers is not particularly limited, and may be a long fiber web formed by a spunbond method, a melt-blown method, a tow opening method, or the like, or may be a short fiber web formed using short fibers (staples and chops) by a carding method, an airlaid method, a wet method, or the like. Among these, from the viewpoint of improving bulkiness and softness, a web formed by the carding method or the airlaid method is preferable, and a web formed by the carding method is more preferable. In the present invention, the term "web" refers to a fiber assembly in a state in which a lot of fibers are entangled, and means a state in which the points at which the heat fusible composite fibers intersect with each other are not fused.

Next, in the web obtained in the web formation step, the points at which the heat fusible composite fibers intersect with each other are fused by heat under no pressure using superheated steam gas. For example, a method in which a nonwoven fabric is continuously obtained by introducing a web into a furnace filled with superheated steam gas by a conveyer for conveying or the like can be exemplified. The term "under no pressure" refers to a state in which no pressure is substantially applied to the web, and when the thickness of the nonwoven fabric is 80% or more of the thickness of the web, this can be determined as "under no pressure".

The temperature of the superheated steam gas is not particularly limited, but may be +0° C. to +30° C. of the melting point or softening point of the low-melting thermoplastic resin constituting the heat fusible composite fibers. In addition, the blowing speed of the superheated steam gas is not particularly limited as long as it is within a range that allows the non-pressure state, but the blowing speed is preferably less than 0.1 m/minute. In addition, the blowing pressure of the superheated steam gas is not particularly limited as long as it is within a range that allows the non-pressure state, but the blowing pressure is preferably less than 0.1 kPa.

The treatment time of the heat fusion step is not particularly limited, but is preferably 60 seconds or shorter, and is more preferably 30 seconds or shorter. When the treatment time is 60 seconds or shorter, it becomes possible to produce a nonwoven fabric with satisfactory productivity.

In the method for producing a nonwoven fabric of the present invention, a heat treatment may be further performed after the heat fusion step for the purpose of preventing the occurrence of lint of the nonwoven fabric. A heat treatment method is not particularly limited, but examples thereof include a through-air treatment of applying a circulating hot air current to the nonwoven fabric, and a floating dryer treatment of applying a hot air current from above and below while floating the nonwoven fabric. In the nonwoven fabric of the present invention, because the points at which the fibers intersect with each other are fused by heat in a state close to a web shape by superheated steam gas, even when the heat treatment is performed using a hot air current or the like in the subsequent step, the occurrence of lint of the nonwoven fabric can be further prevented without impairing the bulk of the nonwoven fabric.

The nonwoven fabric of the present invention can be used for applications to various fiber products, which require bulkiness and high strength, such as absorbent articles such as diapers, napkins, and incontinence pads; sanitary materials such as masks, gowns, and surgical gowns; interior materials such as wall sheets, shoji paper, and flooring; daily life-related materials such as fabric covers, wipers for cleaning, and plastic food waste bags; toiletries products such as disposable toilets and plastic toilet bags; pet supplies such as pet sheets, pet diapers, and pet towels; industrial materials such as wiping materials, filters, cushioning materials, oil adsorbing materials, and ink tank adsorbents; general medical materials; bedding materials; and nursing care products, for example.

EXAMPLES

The present invention will be described in more detail below with reference to examples, but the scope of the present invention is not limited to these.

Evaluation of the performance of the nonwoven fabric of the present invention was performed by the following method.

<Fineness of Heat Fusible Composite Fibers

The fineness of the heat fusible composite fibers was measured according to JIS L 1015.

<Fiber Density of High-Density-Side and Low-Density-Side Surface Layers

Using a laser microscope (VK-X210) manufactured by KEYENCE CORPORATION, the surface layers on both sides of the nonwoven fabric (from the surface of the nonwoven fabric to the depth of 20% of the thickness of the entire nonwoven fabric toward the center in the thickness direction) were scanned to obtain images of both surface layers of the nonwoven fabric with a visual field of 1 mm×1.4 mm. In the obtained image, a line parallel to the width direction (CD direction) of the nonwoven fabric was drawn, and the number of intersections of the line with fibers was counted to determine the number of fibers. The cross-sectional area in the CD direction was defined as the product of the length of the above-mentioned line parallel to the CD direction and the length (length 20% of the thickness of the nonwoven fabric) scanned in the thickness direction with the laser microscope. Then, the obtained number of fibers was divided by the cross-sectional area in the CD direction, and the average value of a total of 9 points of this value was defined as the fiber density in the CD direction (fibers/mm$^2$). Similarly, the number of fibers intersecting a line parallel to the machine direction (MD direction) of the nonwoven fabric was divided by the cross-sectional area in the MD direction, and the average value of a total of 9 points of this value was defined as the fiber density in the MD direction (fibers/mm$^2$). The average value of the obtained fiber densities in the CD and MD directions was defined as the fiber density (fibers/mm$^2$) of the surface layer. The above-mentioned measurement was performed on the surface layers of both sides of the nonwoven fabric. A larger value of the fiber density of the surface layer was defined as the fiber density (fibers/mm$^2$) of the high-density-side surface layer, and a smaller value thereof was defined as the fiber density (fibers/mm$^2$) of the low-density-side surface layer.

<Ratio of Fiber Density of High-Density-Side Surface Layer and Fiber Density of Low-Density-Side Surface Layer>

Using the values of the fiber density of the high-density surface layer side and the fiber density of the low-density surface layer side obtained by the above-mentioned method, the ratio of the fiber density of the high-density-side surface layer and the fiber density of the low-density-side surface layer was calculated by the following formula.

Ratio of fiber density of high-density-side surface layer and fiber density of low-density-side surface layer=fiber density (fibers/mm$^2$) of high-density surface layer side/fiber density (fibers/mm$^2$) of low-density surface layer side <Basis Weight of Nonwoven Fabric>

The weight of the nonwoven fabric cut into 100 mm×100 mm was measured, and the value converted per unit area was defined as the basis weight (g/m$^2$) of the nonwoven fabric.

<Thickness of Nonwoven Fabric>

Using a Digi-Thickness Tester manufactured by Toyo Seiki Seisaku-sho, Ltd. was used to measure the thickness at four points when a pressure of 3.5 g/cm$^2$ was applied with a pressure element (load) having a diameter of 35 mm, and the average value thereof was defined as the thickness (mm) of the nonwoven fabric.

<Specific Volume of Nonwoven Fabric>

From the basis weight (g/m²) and thickness (mm) of the nonwoven fabric, the specific volume of the nonwoven fabric was calculated according to the following formula.

Specific volume (cm³/g)=thickness (mm)/basis weight (g/m²)×1000

<Strength Per Unit Basis Weight of Nonwoven Fabric>

A maximum strength when pulling a sample with a size of 50 mm×150 mm and cut long in the MD direction at a chuck distance of 100 mm and a tensile rate of 100 mm/minute using an Autograph (AGX-J) manufactured by Shimadzu Corporation was defined as the strength of the nonwoven fabric, and the value obtained by dividing this strength by the basis weight of the nonwoven fabric (g/m²) was defined as the strength per unit basis weight of the nonwoven fabric.

<Compression Work Amount of Nonwoven Fabric>

Using a handy compression tester (KES-G5) manufactured by KATO TECH CO., LTD., the compression work amount was measured as follows. First, the nonwoven fabric was placed on a specimen table, and a pressurizer having an area of 2 cm² was pressed into the specimen from above to compress the specimen under conditions of a speed of 1.0 cm/second and a maximum compressive load of 4 gf/cm². The compression work amount was calculated by a numerical value treatment based on the measurement data.

<Evaluation of Lint Resistance>

The lint properties of the surface of the nonwoven fabric was sensory evaluated as follows.

⊚: No tingling feeling or rough feeling was felt.

○: A tingling feeling and a rough feeling were slightly felt, but were not bothersome.

X: A tingling feeling and a rough feeling were felt.

<Absorbency Evaluation>

Absorbency evaluation was performed based on an initial liquid permeation time and a repeated liquid permeation time using artificial menstrual blood (viscosity of 16 cP) having the following composition.

Composition of artificial menstrual blood:
(1) Deionized water: 874.7 parts by weight
(2) Sodium chloride: 10.0 parts by weight
(3) Sodium carbonate: 10.7 parts by weight
(4) Glycerin: 100.0 parts by weight
(5) Carboxymethyl cellulose: 4.6 parts by weight <Evaluation of Initial Liquid Permeation Time and Repeated Liquid Permeation Time>

The nonwoven fabric cut into 100 mm×100 mm was placed on an absorber of 90 mm×90 mm (two sheets of Kimtowels (trade name) manufactured by NIPPON PAPER CRECIA CO., LTD.). Next, a liquid permeable plate (SUS plate having a weight of 450 g, 70 mm×70 mm×12 mm, and an opening of 27 mm in the center portion) was placed on the nonwoven fabric. 3 mL of artificial menstrual blood was added dropwise from a height of 12 mm above the center portion of the opening. The time (liquid permeation time) until the artificial menstrual blood disappeared from the surface of the nonwoven fabric was measured (first time) and defined as the initial liquid permeation time.

After leaving to stand 3 minutes from the completion of the first time liquid permeation measurement, the liquid permeation time was measured again by the same procedure (second time), and this liquid permeation time was defined as the repeated liquid permeation time.

Example 1

As heat fusible composite fibers, concentric sheath-core heat fusible composite fibers which had a fineness of 1.7 dtex and a fiber length of 51 mm and to which a hydrophilic fiber treatment agent was provided were used. In the concentric sheath-core heat fusible composite fibers, polyethylene terephthalate (melting point of 250° C.) was disposed in the core and high-density polyethylene (melting point of 130° C.) was disposed in the sheath at a volume fraction of 50/50.

Next, a 3.9 mm-thick web composed of the heat fusible composite fibers was produced by a carding method and introduced into a furnace filled with superheated steam gas at 140° C. for 10 seconds to obtain a nonwoven fabric. The speed of the superheated steam gas was less than 0.1 m/minute.

Figure 2:
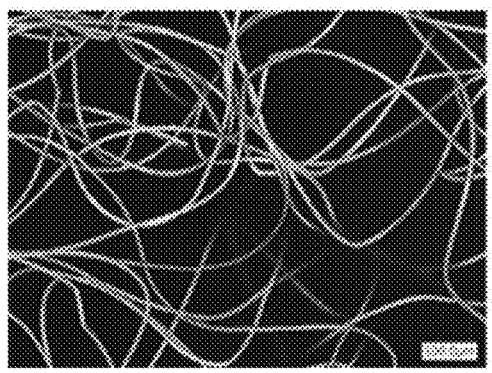
FIG. 2 shows laser micrographs of a surface layer of the nonwoven fabric according to the example of the present invention.
Figure 2:
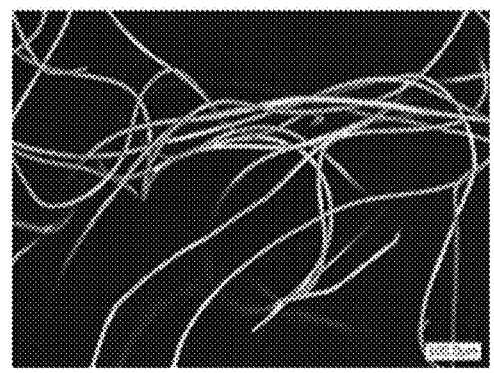

Table 2 shows the physical properties of the obtained nonwoven fabric. In addition, FIG. 1 shows an optical electron micrograph of the cross section of the obtained nonwoven fabric, and FIG. 2 shows laser micrographs of the high-density-side surface layer and the low-density-side surface layer of the nonwoven fabric.

Example 2

As heat fusible composite fibers, concentric sheath-core heat fusible composite fibers which had a fineness of 3.3 dtex and a fiber length of 51 mm and to which a hydrophilic fiber treatment agent was provided were used. In the concentric sheath-core heat fusible composite fibers, polyethylene terephthalate (melting point of 250° C.) was disposed in the core and high-density polyethylene (melting point of 130° C.) was disposed in the sheath at a volume fraction of 70/30.

Next, a 4.8 mm-thick web composed of the heat fusible composite fibers was produced by a carding method and introduced into a furnace filled with superheated steam gas at 140° C. for 10 seconds to obtain a nonwoven fabric. The speed of the superheated steam gas was less than 0.1 m/minute. Table 2 shows the physical properties of the obtained nonwoven fabric.

Example 3

A nonwoven fabric was obtained by further heat-treating the nonwoven fabric obtained in Example 2 with a hot air current at 140° C. and a circulating air velocity of 1.0 m/second using a hot air current circulating dryer. Table 2 shows the physical properties of the obtained nonwoven fabric.

Comparative Example 1

Figure 3:
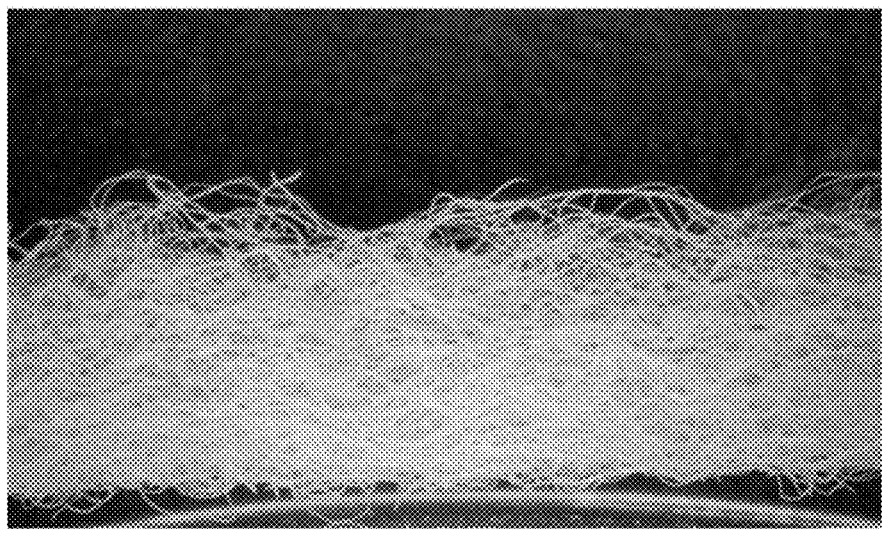
FIG. 3 is an optical micrograph of a cross-section of a nonwoven fabric according to a comparative example of the present invention.
Figure 4:
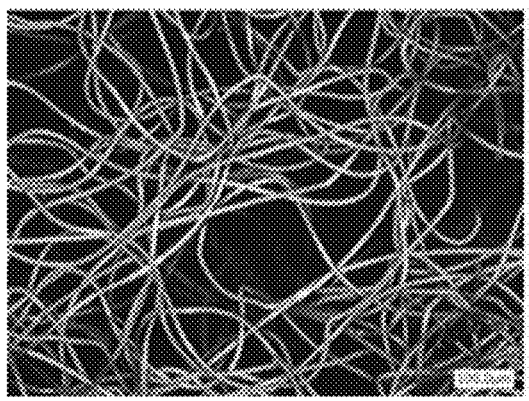
FIG. 4 is a laser micrograph of a surface layer of the nonwoven fabric according to the comparative example of the present invention.
Figure 4:
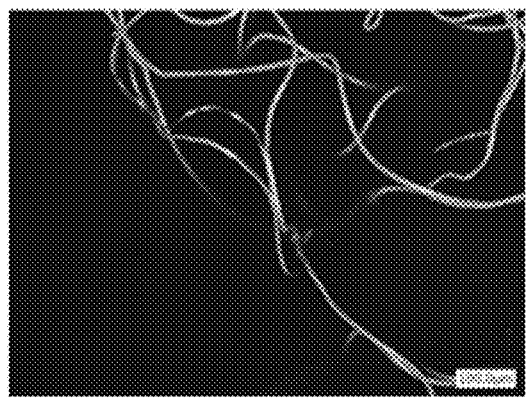

A nonwoven fabric was obtained by treating a web obtained in the same manner as in Example 1 for 10 seconds with a hot air current at 130° C. and a circulating air velocity of 1.0 m/second using a hot air current circulating dryer. Table 2 shows the physical properties of the obtained nonwoven fabric. In addition, FIG. 3 shows an optical electron micrograph of the cross section of the obtained nonwoven fabric, and FIG. 4 shows laser micrographs of the high-density-side surface layer and the low-density-side surface layer of the nonwoven fabric.

Comparative Example 2

A nonwoven fabric was obtained by treating a web obtained in the same manner as in Example 1 for 5 minutes at 145° C. using a hot air current circulating dryer. The speed of the hot air current was less than 0.1 m/minute. Table 2 shows the physical properties of the obtained nonwoven fabric.

Comparative Example 3

A nonwoven fabric was obtained by treating a web obtained in the same manner as in Example 2 for 10 seconds with a hot air current at 130° C. and a circulating air velocity of 1.0 m/second using a hot air current circulating dryer. Table 2 shows the physical properties of the obtained nonwoven fabric.

Table 1 summarizes the production conditions of the nonwoven fabric.

side surface layer and the fiber density of the low-density-side surface layer increased, as a result of which the strength was high, but the bulkiness and softness were impaired, and the liquid permeability with respect to the artificial menstrual blood was also low. In addition, in Comparative Example 2 in which the speed of the hot air current was as low as possible, since the non-pressure state was employed (where the thickness of the nonwoven fabric was 80% or more of the web), the ratio of the fiber density of the high-density-side surface layer and the fiber density of the low-density-side surface layer was small. Therefore, although excellent bulkiness and liquid permeability were obtained, the strength was low, and lint was generated. In addition, the treatment time of the heat fusion step was long,

TABLE 1

|  |  | Example 1 | Example 2 | Example 3 | Comparative Example 1 | Comparative Example 2 | Comparative Example 3 |
|---|---|---|---|---|---|---|---|
| Thermoplastic resin of high melting point component | — | PET | PET | PET | PET | PET | PET |
| Melting point of high melting point component | ° C. | 250 | 250 | 250 | 250 | 250 | 250 |
| Thermoplastic resin of low melting point component | — | HDPE | HDPE | HDPE | HDPE | HDPE | HDPE |
| Melting point of low melting point component | ° C. | 130 | 130 | 130 | 130 | 130 | 130 |
| Volume fraction of low melting point component and high melting point component | volume/volume | 50/50 | 70/30 | 70/30 | 50/50 | 50/50 | 70/30 |
| Composite form | — | Concentric sheath-core | Concentric sheath-core | Concentric sheath-core | Concentric sheath-core | Concentric sheath-core | Concentric sheath-core |
| Fineness | dtex | 1.7 | 3.3 | 3.3 | 1.7 | 1.7 | 3.3 |
| Fiber length | mm | 51 | 51 | 51 | 51 | 51 | 51 |
| Web forming method | — | Carding method | Carding method | Carding method | Carding method | Carding method | Carding method |
| Web thickness | mm | 3.9 | 4.8 | 4.8 | 3.9 | 3.9 | 4.8 |
| Heat medium | — | Superheated steam gas | Superheated steam gas | Superheated steam gas | Circulating hot air current | Circulating hot air current | Circulating hot air current |
| Heat fusion temperature | ° C. | 140 | 140 | 140 | 130 | 145 | 130 |
| Air speed in heat fusion step | m/min | Less than 0.1 | Less than 0.1 | Less than 0.1 | 1.0 | Less than 0.1 | 1.0 |
| Treatment time | sec | 10 | 10 | 10 | 10 | 300 | 10 |
| Heat treatment step | — | Not performed | Not performed | Circulating hot air current | Not performed | Not performed | Not performed |

TABLE 2

|  |  | Example 1 | Example 2 | Example 3 | Comparative Example 1 | Comparative Example 2 | Comparative Example 3 |
|---|---|---|---|---|---|---|---|
| Fiber density of high-density-side surface layer | fibers/mm$^2$ | 15.6 | 9.0 | 9.6 | 54.0 | 18.1 | 23.3 |
| Fiber density of a low-density-side surface layer | fibers/mm$^2$ | 13.2 | 8.7 | 9.1 | 24.0 | 14.2 | 6.9 |
| Ratio of fiber density of high-density-side surface layer and fiber density of low-density-side surface layer | — | 1.18 | 1.03 | 1.05 | 2.25 | 1.27 | 3.38 |
| Basis weight | g/m$^2$ | 30 | 30 | 30 | 30 | 30 | 30 |
| Thickness | mm | 3.6 | 4.4 | 4.3 | 2.4 | 3.7 | 2.8 |
| Specific volume | cm$^3$/g | 120 | 147 | 143 | 80 | 123 | 93 |
| Strength | N/50 mm | 29 | 18 | 21 | 56 | 11 | 40 |
| Strength per unit basis weight | N/50 mm | 0.97 | 0.60 | 0.70 | 1.87 | 0.37 | 1.33 |
| Compression work amount | gf · cm/cm2 | 0.22 | 0.33 | 0.31 | 0.08 | 0.19 | 0.17 |
| Lint resistance | — | ○ | ○ | ◎ | ○ | X | ○ |
| Initial liquid permeation time | sec | 3.3 | 2.4 | 2.7 | 4.3 | 3.1 | 4.7 |
| Repeated liquid permeation time | sec | 7.8 | 5.4 | 5.5 | 11.4 | 6.4 | 8.9 |

In the conventional circulating hot air current treatment (Comparative Examples 1 and 3), since pressure was applied by blowing a hot air current in the heat fusion step (where the thickness of the nonwoven fabric was less than 80% of the web), the ratio of the fiber density of the high-densityand satisfactory productivity was not obtained. In Examples 1 to 3 according to the present invention, since the superheated steam gas was used under no pressure, the ratio of the fiber density of the high-density-side surface layer and the fiber density of the low-density-side surface layer was small.

Therefore, the nonwoven fabric that was bulky, had excellent softness, had sufficient strength, and had excellent liquid permeability with respect to high-viscosity liquids such as artificial menstrual blood was obtained. In addition, the treatment time of the heat fusion step was short, and satisfactory productivity was obtained. In addition, in Example 3 in which the nonwoven fabric obtained by the heat fusion treatment using the superheated steam gas under no pressure was further heat-treated with a circulating hot air current, very excellent lint resistance was obtained.

INDUSTRIAL APPLICABILITY

The nonwoven fabric of the present invention is bulky, has excellent softness, and has high strength, and thus can be suitably used as a surface material for absorbent articles such as disposable diapers and sanitary napkins. In addition, the nonwoven fabric of the present invention can be used for applications to various fiber products, which require bulkiness, softness, and high strength, such as medical supplies such as masks, gowns, and surgical gowns; interior materials such as wall sheets, shoji paper, and flooring; daily life-related materials such as fabric covers, wipers for cleaning, and plastic food waste bags; toiletries products such as disposable toilets and plastic toilet bags; pet supplies such as pet sheets, pet diapers, and pet towels; industrial materials such as wiping materials, filters, cushioning materials, oil adsorbing materials, and ink tank adsorbents; covering materials; poultice bags; bedding materials; and nursing care products.

In addition, according to the production method of the present invention, a nonwoven fabric that is bulky, has excellent softness, and has high strength can be produced with high productivity.

What is claimed is:

1. A nonwoven fabric in which points at which heat fusible composite fibers intersect with each other are fused by heat, the nonwoven fabric comprising:
   a high-density-side surface layer having a fiber density of 5 to 20 fibers/mm$^2$,
   wherein a ratio of the fiber density of the high-density-side surface layer and a fiber density of a low-density-side surface layer of the nonwoven fabric is 1.4 or less, and
   a strength per unit basis weight of the nonwoven fabric is 0.40 N/50 mm or greater, wherein a specific volume is 100 cm$^3$/g or greater.

2. The nonwoven fabric according to claim 1, wherein a compression work amount at a maximum compression load of 4 gf/cm$^2$ is 0.20 gf cm/cm$^2$ or greater.

3. The nonwoven fabric according to claim 1, wherein a fineness of the heat fusible composite fiber is 0.8 to 20 dtex.

4. The nonwoven fabric according to claim 1, wherein a fiber length of the heat fusible composite fiber is 20 to 102 mm.

5. A method for producing a nonwoven fabric, the method comprising:
   forming a web containing heat fusible composite fibers; and
   fusing points at which the heat fusible composite fibers intersect with each other by heat under no pressure using superheated steam gas,
   wherein a blowing pressure of the superheated steam gas is less than 0.1 kPa, and a blowing speed of the superheated steam gas is less than 0.1 m/minute.

6. The method for producing a nonwoven fabric according to claim 5, wherein the step of forming the web is a carding method or an airlaid method.

7. The method for producing a nonwoven fabric according to claim 5, further comprising heat-treating after fusing the heat fusible composite fibers by heat.

8. An absorbent article comprising the nonwoven fabric according to claim 1.

* * * * *